US011987550B2

(12) United States Patent
Kim et al.

(10) Patent No.: US 11,987,550 B2
(45) Date of Patent: May 21, 2024

(54) METHOD FOR PREPARING CROSSLINKER COMPOUND

(71) Applicant: LG Chem, Ltd., Seoul (KR)

(72) Inventors: Ji Eun Kim, Daejeon (KR); Won Taeck Lim, Daejeon (KR); Yongjin Kim, Daejeon (KR); Gicheul Kim, Daejeon (KR); Wonmun Choi, Daejeon (KR); Ki Hyun Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 604 days.

(21) Appl. No.: 16/968,999

(22) PCT Filed: Oct. 7, 2019

(86) PCT No.: PCT/KR2019/013125
§ 371 (c)(1),
(2) Date: Aug. 11, 2020

(87) PCT Pub. No.: WO2020/111496
PCT Pub. Date: Jun. 4, 2020

(65) Prior Publication Data
US 2021/0024451 A1 Jan. 28, 2021

(30) Foreign Application Priority Data
Nov. 28, 2018 (KR) .................. 10-2018-0149736

(51) Int. Cl.
C07C 67/44 (2006.01)
C08J 3/12 (2006.01)
C08J 3/24 (2006.01)
C08K 5/11 (2006.01)

(52) U.S. Cl.
CPC .............. C07C 67/44 (2013.01); C08J 3/12 (2013.01); C08J 3/243 (2013.01); C08K 5/11 (2013.01); C08J 2433/02 (2013.01)

(58) Field of Classification Search
CPC .... C07C 33/044; C07C 33/046; C07C 69/602
See application file for complete search history.

(56) References Cited

U.S. PATENT DOCUMENTS

| 2,992,278 | A | * | 7/1961 | Tedeschi | C07C 29/60 568/903 |
| 3,371,121 | A | * | 2/1968 | Kahn | C07C 29/172 568/861 |
| 4,876,401 | A | * | 10/1989 | Drent | C07C 29/172 568/861 |
| 5,444,170 | A | * | 8/1995 | Vedage | B01J 23/44 568/903 |
| 6,355,702 | B1 | * | 3/2002 | Ober | C08F 222/102 560/98 |
| 6,956,141 | B1 | | 10/2005 | Maas-Brunner et al. | |
| 2003/0166977 | A1 | | 9/2003 | Powell | |
| 2008/0033221 | A1 | | 2/2008 | Hori | |
| 2008/0140037 | A1 | * | 6/2008 | Newman | C08K 5/103 560/190 |
| 2019/0071523 | A1 | | 3/2019 | Kim et al. | |
| 2019/0085103 | A1 | | 3/2019 | Kim et al. | |
| 2019/0091656 | A1 | | 3/2019 | Kim et al. | |
| 2019/0100627 | A1 | | 4/2019 | Kim et al. | |

FOREIGN PATENT DOCUMENTS

| CN | 1247181 A | 3/2000 |
| CN | 104220432 A | 12/2014 |
| CN | 105085168 A | 11/2015 |
| GB | 1167776 A | 10/1969 |
| JP | H07223983 A | 8/1995 |
| JP | 2002121228 A | 4/2002 |
| JP | 2002128961 A | 5/2002 |
| JP | 2004123611 A | 4/2004 |
| JP | 2008522003 A | 6/2008 |
| KR | 20180043143 A | 4/2018 |
| WO | 0191815 A2 | 12/2001 |
| WO | 2007080103 A2 | 7/2007 |
| WO | WO2005094993 A1 | 2/2008 |
| WO | 2018074665 A1 | 4/2018 |

OTHER PUBLICATIONS

Winterbottom, Heterogeneous Catalysis and Fine Chemicals IV, p. 59-66, 1997 (Year: 1997).*
Extended European Search Report for Application No. 19888643.4, dated Mar. 29, 2021, 10 pages.
Gverdtsiteli, I.M. et al: Catalytic Hydration of Acetylene Glycolsi: Investigation of the Rate of Hydrogenation of 2,2,3,6,7,7-HEXAMETHYL-4-0CTYNE-3,6-DIOL and ,5,6,6-TETRAMETHYL-3-HEPTYNE-2,5-DIOL, vol. 2, Jan. 1, 1953 (Jan. 1, 1953), pp. 960-962.
Wikiepia: Walter Reppe, Mar. 16, 2021 (Mar. 16, 2021).
International Search Report for Application No. PCT/KR2019/013125 dated Feb. 5, 2020, 3 pages.
Sajiki, et al., Partial Hydrogenation of Alkynes to cis-Olefins by Using a Novel Pd0-Polyethyleneimine Catalyst. Chemistry—A European Journal. Jun. 9, 2008, pp. 5109-5111, vol. 14, No. 17.
Martin, D., et al,. "Stereoselective Synthesis of 2,2,6,6-Tetrasubstituted Tetrahydropyrans" Synthesis 2001,No. 7, 1013-1022 ISSN0039-7881, Thieme Stuttgart •New York (Jan. 2001). 3 pgs.
Yukio Takagi, N. E. Chemcat Co., Ltd., "Invitation to Rare Metal Powdery Catalyst", Wako Organic Square, Dec. 2014, No. 50. 3 pgs.
Martin, D. et al., "Stereoselective Synthesis of 2,2,6,6-Tetrasubstituted Tetrahydropyrans" Department of Organic Chemistry, Faculty of Chemical Sciences, University of Salamanca, Spain, Synthesis, Jan. 2001, pp. 1013-1022.

(Continued)

Primary Examiner — Robert C Boyle
(74) Attorney, Agent, or Firm — Lerner David LLP

(57) ABSTRACT

The present disclosure relates to a method for preparing a crosslinker compound in which a crosslinker compound capable of using for the production of a super absorbent polymer can be obtained in a higher yield by a simple manner. The crosslinker compound obtained by the above method can be used as a thermally decomposable crosslinker in the process of producing a super absorbent polymer.

7 Claims, No Drawings

(56) References Cited

OTHER PUBLICATIONS

Tedeschi, R. J. "Hydrogenation-Hydrogenolysis Studies of Symmetrically Substituted 1,4-Acetylenic Glycols" The Journal of Organic Chemistry, American Chemical Society, ACS Publications, Jul. 1962, pp. 2398-2402, vol. 27, Issue 7.

European Patent Communication including Written Opinion for Application No. 19888643.4, dated May 12, 2023, pp. 1-8.

* cited by examiner

METHOD FOR PREPARING CROSSLINKER COMPOUND

CROSS-REFERENCE TO RELATED APPLICATIONS

This application is a national phase entry under 35 U.S.C. § 371 of International Application No. PCT/KR2019/013125 filed Oct. 7, 2019, which claims priority from Korean Patent Application No. 10-2018-0149736 filed Nov. 28, 2018, all of which are incorporated herein by reference.

FIELD OF THE INVENTION

The present disclosure relates to a method for preparing a crosslinker compound in which a crosslinker compound capable of using for the production of a super absorbent polymer can be obtained in a higher yield by a simple manner.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for production of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most common cases, these super absorbent polymers have been widely used in the field of sanitary materials such as diapers or sanitary napkins. For these uses, it is necessary to absorb body fluids discharged in large quantities at once within a short time. In general, in order to increase the absorbing amount of the body fluids discharged at once, a method of controlling the crosslink density of the super absorbent polymer to be low is used.

When the overall crosslink density of the super absorbent polymer is controlled to be low, the absorbing amount of the super absorbent polymer can be increased. However, the adhesiveness of the crosslinked polymer increases, which causes problems in the production processes of the super absorbent polymer, such as polymerization and pulverization, and the crosslinked structure becomes loose, the gel strength decreases, and the absorbency under pressure decreases.

Due to the above-mentioned problems, there is a continuous need to develop a super absorbent polymer in which the gel strength of the surface is high and the crosslink density of the interior is controlled to be low. As one means for enabling the development of these super absorbent polymers, a thermally decomposable crosslinker compound represented by the following Chemical Formula 4 is disclosed in Japanese Unexamined Patent Publication No. 2008-522003:

[Chemical Formula 4]

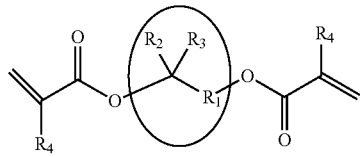

wherein, $R_1$ is a divalent organic group derived from an alkane having 1 to 10 carbon atoms, $R_2$ and $R_3$ are each independently an alkyl group having 1 to 5 carbon atoms, and $R_4$ is hydrogen or a methyl group.

In the crosslinker compound, the functional group at the portion indicated by the circle can be thermally decomposed during the surface crosslinking process in the process of producing the super absorbent polymer. Therefore, when such a crosslinker compound is used as an internal crosslinking agent and subsequent surface crosslinking process is performed at a high temperature, a super absorbent polymer can be produced in which the crosslink density of the surface is greatly improved, and the gel strength of the surface is high, and also the internal crosslink density is controlled to be low by thermal decomposition.

Meanwhile, conventionally, for producing these crosslinker compounds, a method of producing a diol compound through a ring-opening reaction using a Grignard reagent or the like, and then proceeding an esterification reaction with an acyl chloride compound has been generally applied. By the way, in such a conventional method, the ring-opening reaction needs to be carried out in an inert atmosphere such as a nitrogen atmosphere, and there is a difficulty in the process. Furthermore, there is a disadvantage that the yield of the ring-opening reaction is not high, and so the overall yield of the crosslinker compound is lowered.

SUMMARY OF THE INVENTION

Technical Problem

The present disclosure provides a method for preparing a crosslinker compound in which a crosslinker compound capable of using for producing a super absorbent polymer can be obtained in a higher yield by a simple manner.

Further, the present disclosure provides a method for producing a super absorbent polymer using the crosslinker compound obtained by the above preparation method as an internal crosslinking agent, and a super absorbent polymer produced therefrom.

Technical Solution

In one aspect of the present disclosure, there is provided a method for preparing a crosslinker compound which is used as an internal crosslinking agent or a thermally decomposable crosslinker for the production of a super absorbent polymer, the method comprising the steps of:
  hydrogenating a compound of the following Chemical Formula 1 under a noble metal catalyst to form a diol compound of the following Chemical Formula 2; and
  subjecting a diol compound of the following Chemical Formula 2 and a compound of the following Chemical Formula 3 to an esterification reaction to form a compound of the following Chemical Formula 4.

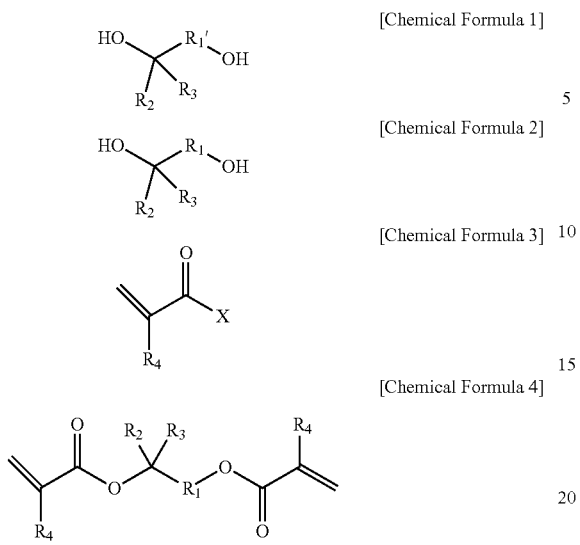

[Chemical Formula 1]

[Chemical Formula 2]

[Chemical Formula 3]

[Chemical Formula 4]

wherein, $R_{1'}$ has a triple bond and is a divalent organic group having 1 to 10 carbon atoms, $R_1$ is a divalent organic group derived from an alkane having 1 to 10 carbon atoms, $R_2$ and $R_3$ are each independently an alkyl group having 1 to 5 carbon atoms, $R_4$ is hydrogen or a methyl group, and X is halogen.

In another aspect of the present disclosure, there is provided a method for producing a super absorbent polymer comprising the steps of:

forming a crosslinker compound by the above-mentioned method;

performing crosslinking polymerization of a water-soluble ethylenically unsaturated monomer having an acidic group of which at least a part is neutralized, in the presence of an internal crosslinking agent including the crosslinker compound to form a hydrogel polymer;

drying, pulverizing and classifying the hydrogel polymer to form a base resin powder; and further cross-linking the surface of the base polymer powder in the presence of a surface crosslinking agent to form a surface cross-linked layer.

In yet another aspect of the present disclosure, there is provided a super absorbent polymer produced by the above-mentioned method.

Hereinafter, a method for preparing a crosslinker compound, and the like according to embodiments of the present disclosure will be described in detail.

According to one embodiment of the present disclosure, there is provided a method for preparing a crosslinker compound which is used as an internal crosslinking agent or a thermally decomposable crosslinker for the production of a super absorbent polymer, the method comprising the steps of:

hydrogenating a compound of the following Chemical Formula 1 under a noble metal catalyst to form a diol compound of the following Chemical Formula 2; and subjecting a diol compound of the following Chemical Formula 2 and a compound of the following Chemical Formula 3 to an esterification reaction to form a compound of the following Chemical Formula 4.

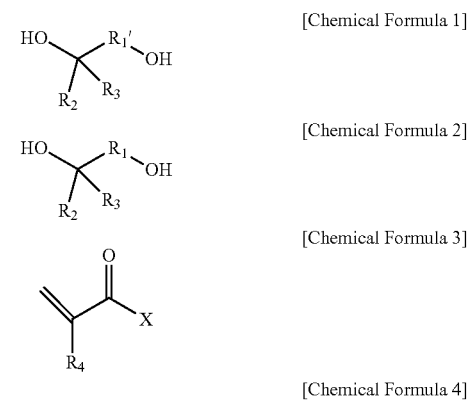

[Chemical Formula 1]

[Chemical Formula 2]

[Chemical Formula 3]

[Chemical Formula 4]

wherein, $R_{1'}$ has a triple bond and is a divalent organic group having 1 to 10 carbon atoms, $R_1$ is a divalent organic group derived from an alkane having 1 to 10 carbon atoms, $R_2$ and $R_3$ are each independently an alkyl group having 1 to 5 carbon atoms, $R_4$ is hydrogen or a methyl group, and X is halogen.

In the method of one embodiment, instead of the ring-opening reaction using a Grignard reagent applied in a conventional method, the hydrogenation reaction of the compound of Chemical Formula 1 having a triple bond is performed to thereby prepare a diol compound of Chemical Formula 2, which is a main precursor for the preparation of the crosslinker compound of Chemical Formula 4, which is then subjected to a conventional esterification reaction to prepare a crosslinker compound of Chemical Formula 4.

As a result of further experiments by the present inventors, it has been found that as the diol compound of Chemical Formula 2 is prepared through the hydrogenation reaction, a crosslinker compound may be prepared in a higher yield. Furthermore, the crosslinker compound can be prepared through continuous preparation processes of compounds having the same reactive group to increase the production amount of the crosslinker compound and so increase the productivity thereof. In addition, in the above preparation method, the hydrogenation reaction does not need to be performed in an inert atmosphere such as a nitrogen atmosphere, and can be performed in an oxygen/air atmosphere, which can reduce the difficulty in the process.

Further, in the conventional method, a thermally decomposable functional group (binding sites of $R_2$ and $R_3$) in Chemical Formula 4 can be introduced into only one moiety, whereas in the method of one embodiment, such a thermally decomposable functional group can also be introduced into $R_1$ (see Example 2 described below).

Therefore, a thermally decomposable crosslinker compound having a more diverse structure can be easily produced in a high yield by the method of one embodiment, and this can be preferably used in the process of producing a super absorbent polymer.

Hereinafter, the preparation process of such a crosslinker compound will be described in more detail for each step.

In the method of the one embodiment, first, the compound of Chemical Formula 1 may be formed. Such compound of Chemical Formula 1 can be prepared, for example, by reacting a compound of the following Chemical Formula 1a with ketone in the presence of a base:

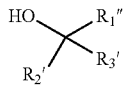

[Chemical Formula 1a]

wherein, $R_{1''}$ has a triple bond at the terminal and is a monovalent organic group having 1 to 9 carbon atoms, and $R_{2'}$ and $R_{3'}$ are each independently hydrogen or an alkyl group having 1 to 5 carbon atoms.

In such reaction step, the triple bond at the terminal of $R_{1''}$ can be linked with a methyl group of ketone to form a compound of Chemical Formula 1. For their suitable reaction, the ketone can be used in an amount of 1 to 4 molar equivalents, or 1.5 to 3 molar equivalents with respect to the compound of Chemical Formula 1a to allow the reaction to proceed.

In such a reaction step, as the base, one or more selected from the group consisting of potassium hydroxide, sodium hydroxide, sodium hydride and potassium hydride may be used, and various other bases can be used without particular limitation.

In addition, the reaction step for forming Chemical Formula 1 can be performed at a temperature of 20 to 50° C. for 1 to 24 hours.

After the compound of Chemical Formula 1 is formed in this manner, it can be hydrogenated under a noble metal catalyst to form a diol compound of Chemical Formula 2. The introduction of such a hydrogenation process allows the method of one embodiment makes it possible to prepare a crosslinker compound in a higher yield by a more simplified method.

In the process of forming these diol compounds, the hydrogenation step may be performed in the presence of a noble metal catalyst including at least one selected from the group consisting of Pd, Pt, Ni and Rh. In addition, it can be performed in the presence of various noble metal catalysts known to be usable for hydrogenation. However, in consideration of the yield or the like of the hydrogenation step, a Pd/C catalyst or the like can be more appropriately used.

Further, the noble metal catalyst for the hydrogenation may be used in an amount of 0.1 to 5 mol %, or 0.5 to 3 mol % with respect to the compound of Chemical Formula 1, whereby the diol compound of Chemical Formula 2 can be efficiently obtained in a higher yield.

And, the hydrogenation step may be performed at a temperature of 10 to 50° C., and it can be performed in the presence of conventional solvents applied to the hydrogenation step, for example, one or more solvents selected from the group consisting of ethyl acetate, methanol, isopropanol, and tetrahydrofuran.

Meanwhile, after forming the diol compound of Chemical Formula 2 through the hydrogenation step, the acryloyl halide compound of Chemical Formula 3 may be subjected to an esterification reaction to prepare a crosslinker compound of Chemical Formula 4.

This esterification step can be performed in the presence of an amine-based base selected from the group consisting of triethylamine, dimethylaminopyridine, diisopropylethylamine, and 1,8-diazabicyclo[5,4,0]undec-7-ene. Of course, it can also be performed in the presence of various amine-based bases. Further, as the acryloyl halide compound of Chemical Formula 3, typically, an acryloyl chloride compound can be used to obtain a crosslinker compound in a higher yield.

Specific reaction conditions and methods of the esterification reaction step are also described in Examples below, and may be in accordance with conventional esterification reaction conditions and methods.

According to the method of one embodiment described above, the crosslinker compound of Chemical Formula 4 may be prepared in high yield, and such a crosslinker compound can be preferably applied as an internal crosslinking agent that can be thermally decomposed in the production process of the super absorbent polymer.

For proper use as such an internal crosslinking agent, in Chemical Formula 4, $R_1$ is a divalent organic group derived from an alkane having 1 to 10 carbon atoms, and $R_2$ is hydrogen or a methyl group. At this time, the alkane may be a linear, branched or cyclic alkane, and the divalent organic group derived from such alkane may be a divalent organic group in which two hydrogens are removed from one carbon, or a divalent organic group in which one hydrogen is respectively removed from mutually different carbons. Specifically, the $R_1$ may be methane-1,1-diyl, ethane-1,2-diyl, ethane-1,1-diyl, propane-1,3-diyl, propane-1,2-diyl, propane-1,1-diyl, n-butane-1,4-diyl, n-butane-1,3-diyl, n-butane-1,2-diyl, n-butane-1,1-diyl, 2-methylpropane-1,3-diyl, 2-methylpropane-1,2-diyl, 2-methylpropane-1,1-diyl, 2-methylbutane-1,4-diyl, 2-methylbutane-2,4-diyl, 2-methylbutane-3,4-diyl, 2-methylbutane-4,4-diyl, 2-methylbutane-1,3-diyl, 2-methylbutane-1,2-diyl, 2-methylbutane-1,1-diyl or 2-methylbutane-2,3-diyl.

Among them, the $R_1$ in Chemical Formula 4 may be methane-1,1-diyl, propane-1,3-diyl, propane-1,2-diyl, propane-1,1-diyl, n-butane-1,4-diyl, n-butane-1,3-diyl, n-butane-1,2-diyl, n-butane-1,1-diyl, 2-methylpropane-1,3-diyl, 2-methylpropane-1,2-diyl, 2-methylpropane-1,1-diyl, 2-methylbutane-1,4-diyl, 2-methylbutane-2,4-diyl, 2-methylbutane-3,4-diyl, 2-methylbutane-4,4-diyl, 2-methylbutane-1,3-diyl, 2-methylbutane-1,2-diyl, 2-methylbutane-1,1-diyl or 2-methylbutane-2,3-diyl. Specifically, the $R_1$ in Chemical Formula 4 may be methane-1,1-diyl, propane-1,3-diyl or propane-1,2-diyl. More specifically, the $R_1$ in Chemical Formula 4 may be propane-1,3-diyl or propane-1,2-diyl.

The compound in which the $R_1$ in Chemical Formula 4 is the divalent organic groups listed above may provide an internal crosslinked structure that can easily adjust the resolution by thermal energy, and after decomposition, by-products or water-soluble components that change the overall physical properties of the super absorbent polymer may not be produced.

The production method of the super absorbent polymer using the above-mentioned crosslinker compound may include, for example, the steps of:
  forming a crosslinker compound by the method of one embodiment described above;
  performing crosslinking polymerization of a water-soluble ethylenically unsaturated monomer having an acidic group of which at least a part is neutralized, in the presence of an internal crosslinking agent including the crosslinker compound to form a hydrogel polymer;
  drying, pulverizing and classifying the hydrogel polymer to form a base resin powder; and
  further cross-linking the surface of the base polymer powder in the presence of a surface crosslinking agent to form a surface cross-linked layer.

In this method, after the compound of Chemical Formula 4 forms an internal crosslinked structure during the cross-linking polymerization process, a decomposition reaction can be caused by heat treatment in a subsequent additional crosslinking process. As a result, the super absorbent polymer prepared by the above method can have an internal crosslink density controlled to be relatively low, while having a high surface crosslink density and gel strength due to a high additional crosslinking reaction. Therefore, such a super absorbent polymer simultaneously exhibits excellent gel strength and absorbency under pressure together with high absorbency, and thus can be used for various hygienic materials.

On the other hand, the production method of the super absorbent polymer can be in accordance with the conventional production method and conditions of the super absorbent polymer disclosed in Japanese Unexamined Patent Publication No. 2008-522003, etc., except that a crosslinker compound prepared by the method of one embodiment is used.

Advantageous Effects

As described above, according to the present disclosure, a crosslinker compound of Chemical Formula 4 that can be used for the production of a super absorbent polymer can be obtained in a high yield by a simple method.

DETAILED DESCRIPTION OF THE EMBODIMENTS

Hereinafter, the action and effect of the present disclosure will be described with reference to examples. However, these examples are given for illustrative purposes only and are not intended to limit the scope of the present disclosure thereto.

Example 1: Preparation of Crosslinker Compound

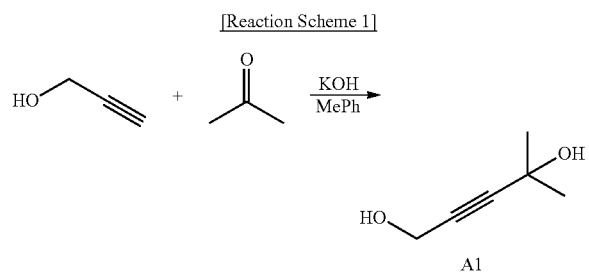

[Reaction Scheme 1]

To a 250 mL round bottom flask, 20.0 g (357 mmol) of propazyl alcohol was added, and 75 mL of toluene was added. 24.02 g (428.1 mmol, 1.2 eq) of potassium hydroxide was further added, 62.16 g (1.07 mol, 3.0 eq) of acetone was slowly added for 2 hours, and the temperature was adjusted so as not to rise above 50° C. After the addition of acetone was completed and the reaction was performed at 50° C. for 1 hour, the temperature was slowly raised to room temperature, and the mixture was reacted for 12 hours. When the reaction was completed, 25.7 g (428.1 mmol) of acetic acid and 50 mL of water were added to prepare a toluene layer. To the mixed solution of acetic acid and water, 40 mL of ethyl acetate was added, diluted, and extracted twice. Magnesium sulfate was added to the extracted ethyl acetate layer to remove water, and the resulting mixture was filtered using a celite pad. The filtered ethyl acetate solution was concentrated to obtain 32.5 g (yield: 80%) of A1 of Reaction Scheme 1.

$^1$H NMR (500 MHz, CDCl$_3$) 4.2 (2H, s), 1.25 (6H, s)

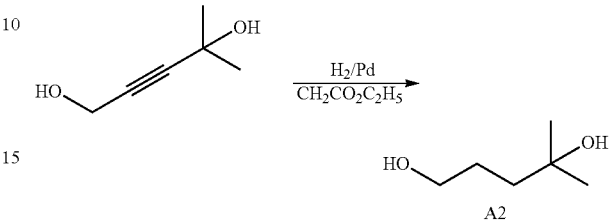

[Reaction Scheme 2]

30.0 g (263 mmol) of A1 was added to an autoclave, and 60 mL of ethyl acetate was added. 0.285 g (2.63 mmol, 1 mol %) of Pd/C catalyst was further added, and hydrogen gas was slowly added so that it becomes 10 bar. When the reaction was performed at room temperature and hydrogen gas was consumed, it was allowed to continuously maintain 10 bar. When the hydrogenation reaction was performed for 12 hours and then the reaction was completed, hydrogen gas was removed, and the autoclave was opened. The resulting mixture was filtered using a celite pad. The filtered ethyl acetate solution was concentrated to obtain 25.5 g (yield: 90%) of A2 of Reaction Scheme 2.

$^1$H NMR (500 MHz, CDCl$_3$) 3.67 (2H, t), 2.11 (2H, br), 1.68 (2H, m), 1.60 (2H, d), 1.25 (6H, s)

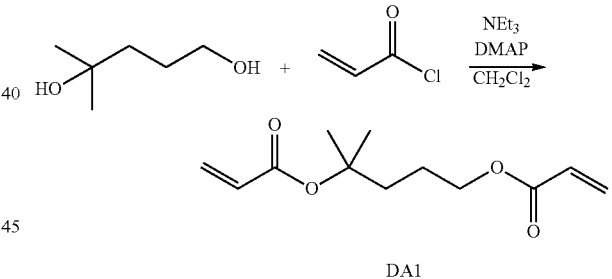

[Reaction Scheme 3]

To a 250 mL round bottom flask, 20.0 g (169 mmol) of the product A2 was added, and 120 mL of methylene chloride was added. 51.38 g (508 mmol, 3.0 eq) of triethylamine and 2.07 g (16.92 mmol, 0.1 eq) of 4-dimethylaminopyridine were further added, and a mixed solution of 45.95 g (507.7 mmol, 3.0 eq) of acryloyl chloride and 50 mL of methylene chloride was slowly added at 0° C. for 2 hours. After reacting at 0° C. for 1 hour, the temperature was slowly raised to room temperature, and the mixture was reacted for 12 hours. When the reaction was completed, the solvent methylene chloride was removed under reduced pressure. 200 mL of n-hexane was added and diluted, and washed twice with 200 mL of water. 20 mL of acetonitrile was added to the extracted n-hexane solution and washed. Magnesium sulfate was added to the final extracted n-hexane solution to remove water, and the resulting mixture was filtered using a celite pad. The filtered n-hexane solution was concentrated to obtain 23.4 g (yield: 82.8%) of the crosslinker compound DA1 of Reaction Scheme 3.

$^1$H NMR (500 MHz, CDCl$_3$) 6.43 (1H, dd), 6.32 (1H, dd), 6.04 (1H, dd), 5.84 (1H, dd), 5.77 (1H, dd), 4.17 (2H, t), 1.88 (2H, m), 1.75 (2H, m), 1.50 (6H, s)

Example 2: Preparation of Crosslinker Compound

[Reaction Scheme 4]

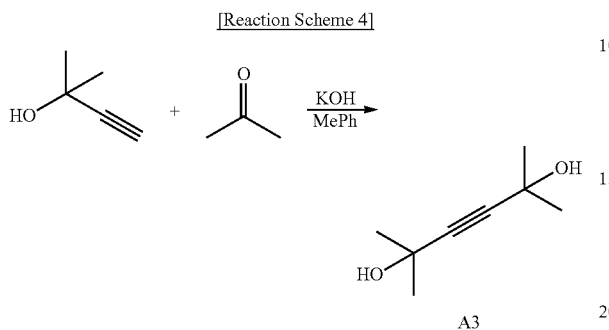

A3

To a 250 mL round bottom flask, 30.0 g (357 mmol) of 2-methyl-3-butynol was added, and 75 mL of toluene was added. 24.02 g (428.1 mmol, 1.2 eq) of potassium hydroxide was further added and 62.16 g (1.07 mol, 3.0 eq) of acetone was slowly added for 2 hours, and the temperature was adjusted so as not to rise above 50° C. After the addition of acetone was completed and the reaction was performed at 50° C. for 1 hour, the temperature was slowly raised to room temperature, and the mixture was reacted for 12 hours. When the reaction was completed, 25.7 g (428.1 mmol) of acetic acid and 50 mL of water were added to prepare a toluene layer. To the mixed solution of acetic acid and water, 40 mL of ethyl acetate was added, diluted, and extracted twice. Magnesium sulfate was added to the extracted ethyl acetate layer to remove water, and the resulting mixture was filtered using a celite pad. The filtered ethyl acetate solution was concentrated to obtain 43.6 g (yield: 86%) of A3 of Reaction Scheme 4.

$^1$H NMR (500 MHz, CDCl$_3$) 1.51 (12H, s)

[Reaction Scheme 5]

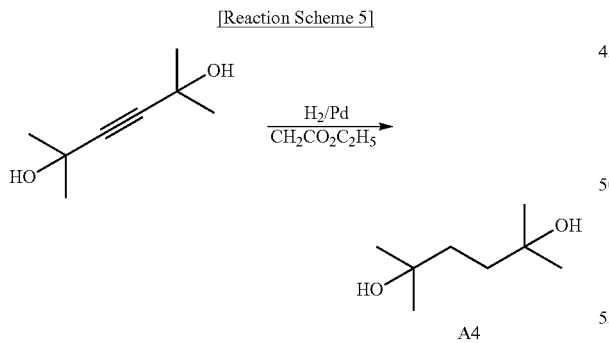

A4

37.4 g (263 mmol) of A3 was added to an autoclave, and 60 mL of ethyl acetate was added. 0.285 g (2.63 mmol, 1 mol %) of Pd/C catalyst was further added, and hydrogen gas was slowly added so that it becomes 10 bar. When the reaction was performed at room temperature and hydrogen gas was consumed, it was allowed to continuously maintain 10 bar. When the hydrogenation reaction was performed for 12 hours and then the reaction was completed, hydrogen gas was removed, and the autoclave was opened. The resulting mixture was filtered using a celite pad. The filtered ethyl acetate solution was concentrated to obtain 32.3 g (yield: 84%) of A4 of Reaction Scheme 5.

$^1$H NMR (500 MHz, CDCl$_3$) 2.89 (2H, bs), 1.71 (4H, s), 1.25 (12H, s)

[Reaction Scheme 6]

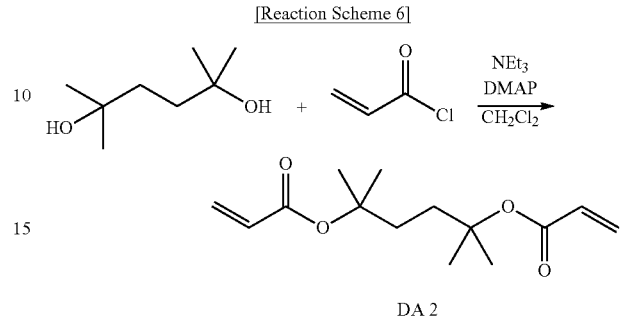

DA 2

To a 250 mL round bottom flask, 24.7 g (169 mmol) of the product A4 was added, and 120 mL of methylene chloride was added. 51.38 g (508 mmol, 3.0 eq) of triethylamine and 2.07 g (16.92 mmol, 0.1 eq) of 4-dimethylaminopyridine were further added, and a mixed solution of 45.95 g (507.7 mmol, 3.0 eq) of acryloyl chloride and 50 mL of methylene chloride was slowly added at 0° C. for 2 hours. After reacting at 0° C. for 1 hour, the temperature was slowly raised to room temperature, and the mixture was reacted for 12 hours. When the reaction was completed, the solvent methylene chloride was removed under reduced pressure. 200 mL of n-hexane was added and diluted, and washed twice with 200 mL of water. 20 mL of acetonitrile was added to the extracted n-hexane solution and washed. Magnesium sulfate was added to the final extracted n-hexane solution to remove water, and the resulting mixture was filtered using a celite pad. The filtered n-hexane solution was concentrated to obtain 27.5 g (yield: 84%) of the crosslinker compound DA2 of Reaction Scheme 6.

$^1$H NMR (500 MHz, CDCl$_3$) 6.43 (2H, dd), 6.32 (2H, dd), 6.04 (2H, dd), 1.93 (s, 4H), 1.51 (s, 12H)

Example 3: Preparation of Crosslinker Compound

[Reaction Scheme 7]

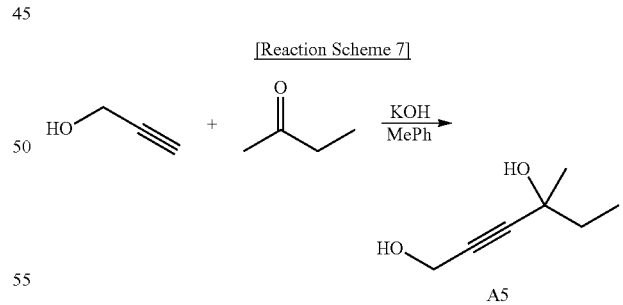

A5

To a 250 mL round bottom flask, 20.0 g (357 mmol) of propazyl alcohol was added, and 75 mL of toluene was added. 24.02 g (428.1 mmol, 1.2 eq) of potassium hydroxide was further added, 77.17 g (1.07 mol, 3.0 eq) of butan-2-one was slowly added for 2 hours, and the temperature was adjusted so as not to rise above 50° C. After the addition of ketone was completed and the reaction was performed at 50° C. for 1 hour, the temperature was slowly raised to room temperature, and the mixture was reacted for 12 hours. When the reaction was completed, 25.7 g (428.1 mmol) of acetic acid and 50 mL of water were added to prepare a toluene layer. To the mixed solution of acetic acid and water, 40 mL of ethyl acetate was added, diluted, and extracted twice. Magnesium sulfate was added to the extracted ethyl acetate layer to remove water, and the resulting mixture was filtered using a celite pad. The filtered ethyl acetate solution was concentrated to obtain 38.9 g (yield: 85%) of A5 of Reaction Scheme 7.

$^1$H NMR (500 MHz, CDCl$_3$) 4.35 (s, 2H), 2.84 (bs, 2H), 1.42-1.72 (m, 2H), 1.41 (s, 3H), 1.36 (t, 3H)

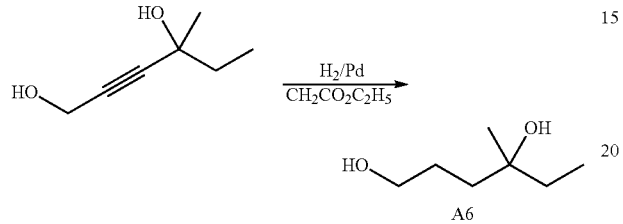

33.7 g (263 mmol) of A5 was added to an autoclave, and 60 mL of ethyl acetate was added. 0.285 g (2.63 mmol, 1 mol %) of Pd/C catalyst was further added, and hydrogen gas was slowly added so that it becomes 10 bar. When the reaction was performed at room temperature and hydrogen gas was consumed, it was allowed to continuously maintain 10 bar. When the hydrogenation reaction was performed for 12 hours and then the reaction was completed, hydrogen gas was removed, and the autoclave was opened. The resulting mixture was filtered using a celite pad. The filtered ethyl acetate solution was concentrated to obtain 30.6 g (yield: 88%) of A6 of Reaction Scheme 8.

$^1$H NMR (500 MHz, CDCl$_3$) 4.35 (bs, 1H, 1-OH), 3.95 (s, 1H, 2-OH), 3.42 (m, 2H), 1.29-1.43 (m, 4H), 0.71 (t, 3H)

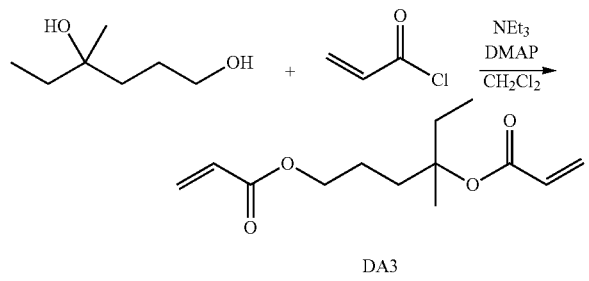

To a 250 mL round bottom flask, 22.4 g (169 mmol) of the product A6 was added, and 120 mL of methylene chloride was added. 51.38 g (508 mmol, 3.0 eq) of triethylamine and 2.07 g (16.92 mmol, 0.1 eq) of 4-dimethylaminopyridine were further added, and a mixed solution of 45.95 g (507.7 mmol, 3.0 eq) of acryloyl chloride and 50 mL of methylene chloride was slowly added at 0° C. for 2 hours. After reacting at 0° C. for 1 hour, the temperature was slowly raised to room temperature, and the mixture was reacted for 12 hours. When the reaction was completed, the solvent methylene chloride was removed under reduced pressure. 200 mL of n-hexane was added and diluted, and washed twice with 200 mL of water. 20 mL of acetonitrile was added to the extracted n-hexane solution and washed. Magnesium sulfate was added to the final extracted n-hexane solution to remove water, and the resulting mixture was filtered using a celite pad. The filtered n-hexane solution was concentrated to obtain 28.9 g (yield: 71%) of the crosslinker compound DA3 of Reaction Scheme 9.

$^1$H NMR (500 MHz, CDCl$_3$) 6.43 (2H, dd), 6.32 (2H, dd), 6.04 (2H, dd), 4.2 (t, 2H), 1.29-1.43 (m, 6H), 1.2 (s, 3H), 0.91 (t, 3H)

Comparative Example 1: Preparation of Crosslinker Compound

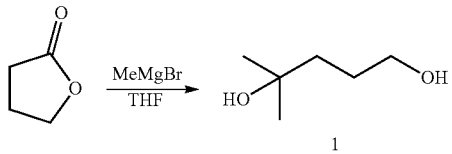

To a 1 L round bottom flask, 25.0 g (290.4 mmol) of γ-butyrolactone was added, and 290 mL (1M) of tetrahydrofuran (THF) was added to the flask. 242 mL of methyl magnesium bromide solution (3M in diethyl ether, 2.5 eq) was added slowly at 0° C., and care was taken not to increase the temperature. When the addition of the methyl magnesium bromide solution at 0° C. was completed, the temperature was raised to room temperature, and the mixture was reacted for 12 hours or more under a nitrogen atmosphere. When the reaction was completed, tetrahydrofuran was removed by distillation under reduced pressure, diluted with 125 mL of ethyl acetate, and washed with 125 mL of water. The product was extracted by adding 125 mL of ethyl acetate to the washed water.

Magnesium sulfate was added to the ethyl acetate solution to remove water, and then resulting mixture was filtered using a celite pad. The filtered ethyl acetate solution was concentrated to obtain 24.7 g (72%) of the product 1 of Chemical Scheme 10.

$^1$H NMR (500 MHz, CDCl$_3$) 3.67 (2H, t), 2.11 (2H, br), 1.68 (2H, m), 1.60 (2H, d), 1.25 (6H, s)

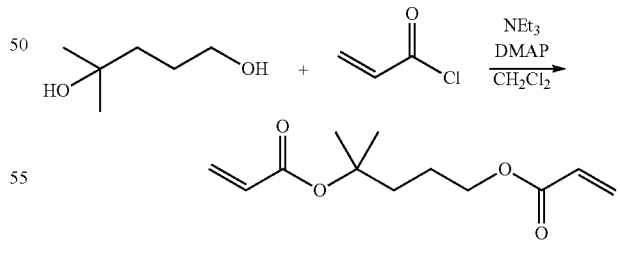

To a 250 mL round bottom flask, 20.0 g (169 mmol) of the product 1 was added, and 120 mL of methylene chloride was added. 51.38 g (508 mmol, 3.0 eq) of triethylamine and 2.07 g (16.92 mmol, 0.1 eq) of 4-dimethylaminopyridine were further added, and a mixed solution of 45.95 g (507.7 mmol, 3.0 eq) of acryloyl chloride and 50 mL of methylene chloride was slowly added at 0° C. for 2 hours. After reacting at 0°

C. for 1 hour, the temperature was slowly raised to room temperature, and the mixture was reacted for 12 hours. When the reaction was completed, the solvent methylene chloride was removed under reduced pressure. 200 mL of n-hexane was added and diluted, and washed twice with 200 mL of water. 20 mL of acetonitrile was added to the extracted n-hexane solution and washed. Magnesium sulfate was added to the final extracted n-hexane solution to remove water, and the resulting mixture was filtered using a celite pad. The filtered n-hexane solution was concentrated to obtain 23.4 g (yield: 61%) of the crosslinker compound DA2 of Reaction Scheme 11.

$^1$H NMR (500 MHz, CDCl$_3$) 6.43 (1H, dd), 6.32 (2H, dd), 6.13 (1H, dd), 6.04 (1H, dd), 5.84 (1H, dd), 5.77 (1H, dd), 4.17 (2H, t), 1.88 (2H, m), 1.75 (2H, m), 1.50 (6H, s)

Comparative Example 2: Preparation of Crosslinker Compound

[Reaction Scheme 12]

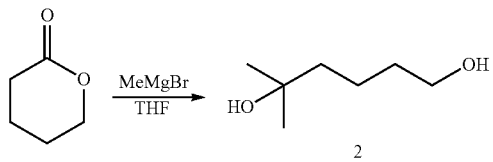

To a 1 L round bottom flask, 30.0 g (299.7 mmol) of δ-valerolactone was added, and 300 mL (1M) of tetrahydrofuran (THF) was added to the flask. 250 mL of methyl magnesium bromide solution (3M in diethyl ether, 2.5 eq) was added slowly at 0° C., and care was taken not to increase the temperature. When the addition of the methyl magnesium bromide solution at 0° C. was completed, the temperature was raised to room temperature, and the mixture was reacted for 12 hours or more under a nitrogen atmosphere. When the reaction was completed, tetrahydrofuran was removed by distillation under reduced pressure, diluted with 150 mL of ethyl acetate, and washed with 150 mL of water. The product was extracted by adding 150 mL of ethyl acetate to the washed water. Magnesium sulfate was added to the ethyl acetate solution to remove water, and then resulting mixture was filtered using a celite pad. The filtered ethyl acetate solution was concentrated to obtain 30.9 g (78%) of the product 2 of Chemical Scheme 12.

$^1$H NMR (500 MHz, CDCl$_3$) 3.63 (2H, t), 2.11 (2H, br), 1.59-1.40 (6H, m), 1.20 (6H, s)

[Reaction Scheme 13]

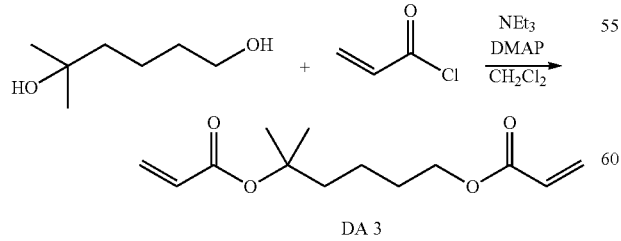

DA 3

To a 250 mL round bottom flask, 22.4 g (169 mmol) of the product 2 was added, and 120 mL of methylene chloride was added. 51.38 g (508 mmol, 3.0 eq) of triethylamine and 2.07 g (16.92 mmol, 0.1 eq) of 4-dimethylaminopyridine were further added, and a mixed solution of 45.95 g (507.7 mmol, 3.0 eq) of acryloyl chloride and 50 mL of methylene chloride was slowly added at 0° C. for 2 hours. After reacting at 0° C. for 1 hour, the temperature was slowly raised to room temperature, and the mixture was reacted for 12 hours. When the reaction was completed, the solvent methylene chloride was removed under reduced pressure. 250 mL of n-hexane was added and diluted, and washed twice with 200 mL of water. 20 mL of acetonitrile was added to the extracted n-hexane solution and washed. Magnesium sulfate was added to the final extracted n-hexane solution to remove water, and the resulting mixture was filtered using a celite pad. The filtered n-hexane solution was concentrated to obtain 26.1 g (yield: 64%) of the crosslinker compound DA3 of Reaction Scheme 13.

$^1$H NMR (500 MHz, CDCl$_3$) 6.43 (1H, dd), 6.32 (2H, dd), 6.13 (1H, dd), 6.04 (1H, dd), 5.84 (1H, dd), 5.77 (1H, dd), 4.17 (2H, t), 1.88 (2H, m), 1.75-1.52 (4H, m), 1.50 (6H, s)

Referring to the Examples and Comparative Examples, it was confirmed that in the Examples, higher yields can be exhibited, especially in the process of preparing the diol compound of Chemical Formula 2, In contrast, it was confirmed that in the Comparative Examples, in the process of preparing the diol compound of Chemical Formula 2, a relatively low yield is exhibited even while requiring to proceed under a nitrogen atmosphere.

What is claimed is:
1. A method for preparing a crosslinker compound which is used as an internal crosslinking agent or a thermally decomposable crosslinker for production of a super absorbent polymer, the method comprising the steps of:
   reacting a compound of Chemical Formula 1a with a ketone in the presence of a base to form a compound of Chemical Formula 1,
   hydrogenating the compound of Chemical Formula 1 under a catalyst in the presence of one or more solvents selected from the group consisting of ethyl acetate, methanol, and tetrahydrofuran to form a compound of Chemical Formula 2, wherein the catalyst consists of Pd/C, and is used in an amount of 0.1 to 5 mol % with respect to the compound of Chemical Formula 1, and
   subjecting the compound of Chemical Formula 2 and a compound of Chemical Formula 3 to an esterification reaction to form a compound of Chemical Formula 4:

[Chemical Formula 1a]

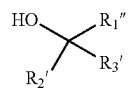

[Chemical Formula 1]

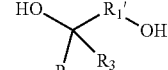

[Chemical Formula 2]

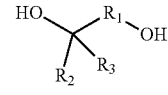

[Chemical Formula 3]

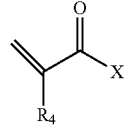

-continued

[Chemical Formula 4]

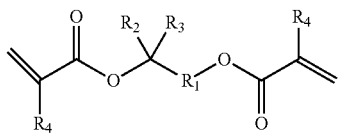

wherein, $R_{1'}$ has a triple bond and is a divalent organic group having 2 to 10 carbon atoms, $R_1$ is a divalent organic group comprising an alkyl group having 2 to 10 carbon atoms, $R_2$ and $R_3$ are each independently an alkyl group having 1 to 5 carbon atoms, $R_4$ is hydrogen or a methyl group, X is halogen, $R_{1''}$ has a triple bond at the terminal and is a monovalent organic group having 2 to 9 carbon atoms, and $R_{2'}$ and $R_{3'}$ are each independently hydrogen or an alkyl group having 1 to 5 carbon atoms.

2. The method for preparing a crosslinker compound according to claim 1, wherein the base comprises one or more selected from potassium hydroxide, sodium hydroxide, sodium hydride or potassium hydride.

3. The method for preparing a crosslinker compound according to claim 1, wherein the esterification step is performed in the presence of an amine-based base selected from the group consisting of triethylamine, dimethylaminopyridine, diisopropylethylamine, and 1,8-diazabicyclo[5,4,0]undec-7-ene.

4. The method for preparing a crosslinker compound according to claim 1, wherein in Chemical Formula 4, $R_1$ is propane-1,3-diyl, propane-1,2-diyl, n-butane-1,4-diyl, n-butane-1,3-diyl, n-butane-1,2-diyl, 2-methylpropane-1,3-diyl, 2-methylpropane-1,2-diyl, 2-methylbutane-1,4-diyl, 2-methylbutane-2,4-diyl, 2-methylbutane-3,4-diyl, 2-methylbutane-1,3-diyl, 2-methylbutane-1,2-diyl, or 2-methylbutane-2,3-diyl.

5. The method for preparing a crosslinker compound according to claim 1, wherein the ketone is used in an amount of 1 to 4 molar equivalents with respect to the compound of Chemical Formula 1a.

6. The method for preparing a crosslinker compound according to claim 1, wherein the step of reacting the compound of Chemical Formula 1a with the ketone is performed at a temperature of 20 to 50° C. for 1 to 24 hours.

7. The method for preparing a crosslinker compound according to claim 1, wherein the hydrogenation step is performed at a temperature of 10 to 50° C.

* * * * *